(12) United States Patent
German et al.

(10) Patent No.: US 11,225,459 B2
(45) Date of Patent: Jan. 18, 2022

(54) SUBSTITUTED BISPHENYLALKYLUREA COMPOUNDS AND METHODS

(71) Applicant: TEXAS TECH UNIVERSITY SYSTEM, Lubbock, TX (US)

(72) Inventors: Nadezhda German, Amarillo, TX (US); Mikelis Constantinos, Amarillo, TX (US)

(73) Assignee: Texas Tech University System, Lubbock, TX (US)

(*) Notice: Subject to any disclaimer, the term of this patent is extended or adjusted under 35 U.S.C. 154(b) by 22 days.

(21) Appl. No.: 16/637,695

(22) PCT Filed: Aug. 9, 2018

(86) PCT No.: PCT/US2018/046146
§ 371 (c)(1),
(2) Date: Feb. 7, 2020

(87) PCT Pub. No.: WO2019/032924
PCT Pub. Date: Feb. 14, 2019

(65) Prior Publication Data
US 2020/0181069 A1 Jun. 11, 2020

Related U.S. Application Data

(60) Provisional application No. 62/543,336, filed on Aug. 9, 2017.

(51) Int. Cl.
*C07C 275/30* (2006.01)
(52) U.S. Cl.
CPC .................. *C07C 275/30* (2013.01)

(58) Field of Classification Search
None
See application file for complete search history.

(56) References Cited

U.S. PATENT DOCUMENTS

2008/0125424 A1* 5/2008 DePrez .................... A61P 9/12
514/233.8
2013/0115202 A1 5/2013 Theoharides

FOREIGN PATENT DOCUMENTS

WO 2010068453 A1 6/2010

OTHER PUBLICATIONS

Maria B. Passani et al.: "Histamine and neuroinflammation: insights from murine experimental autoimmune encephalomyelitis", Frontiers in Systems Neuroscience, vol. 6, Jan. 1, 2012 (Jan. 1, 2012), XP055517295, DOI: 10.3389/fnsys.2012.00032.
(Continued)

*Primary Examiner* — Sudhakar Katakam
*Assistant Examiner* — Jennifer C Sawyer
(74) *Attorney, Agent, or Firm* — Dickinson Wright PLLC; Kristopher Lance Anderson

(57) ABSTRACT

Disclosed is a composition and method for a therapeutic treatment that is able to combat neuroinflammation caused by diseases and disorders such as Alzheimer's disease, Parkinson's disease, and traumatic brain injury. The class of urea compounds acts by blocking at targeted receptors in the brain that contribute to the increase in inflammation. Combinations of receptors, H1 receptor, H2 receptor, dopamine transporter (DAT), and/or 5HT3C receptor, are individually and/or collectively inhibited by the same compositions of the present disclosure, and this ability leads to a decrease in brain edema. The DAT inhibitory effects additionally maintains dopamine levels in a patient.

5 Claims, 6 Drawing Sheets

(56) References Cited

OTHER PUBLICATIONS

A. V. Smolobochkin et al.: "Synthesis of functionalized diarylbutane derivatives by the reaction of 2-methylresorcinol with [gamma]-ureidoacetals", Russian Journal of General Chemistry., vol. 85, No. 7, Jul. 1, 2015 (Jul. 1, 2015), pp. 1779-1782, XP055517242, RU, ISSN: 1070-3632, DOI: 10.1134/S1070363215070361.
International Search Authority, International Search Report and Written Opinion for PCT/US18/046146 dated Oct. 31, 2018, 18 pages.
International Search Authority, International Preliminary Report on Patentability for PCT/US18/046146 dated Feb. 20, 2020, 11 pages.

\* cited by examiner

SUBSTITUTED BISPHENYLALKYLUREA COMPOUNDS AND METHODS

CROSS-REFERENCE TO RELATED APPLICATIONS

This application is a 35 U.S.C § 371 national application of International PCT Application Serial No. PCT/US18/46146, filed Aug. 9, 2018, published as WO 2019/032924, published on Feb. 14, 2019, and entitled "Substituted Bisphenylalkylurea Compounds And Methods", which designated the United States, and which claims priority to U.S. Provisional Application Ser. No. 62/543,336 filed Aug. 9, 2017 entitled "Substituted Bisphenylalkylurea Compounds And Methods". These applications are incorporated herein by reference in their entirety.

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

TECHNICAL FIELD

The present disclosure relates in general to the field of therapeutic treatment. In particular, the present disclosure provides for a novel class of chemical compounds with neuroprotective, anti-inflammatory properties. The disclosed compounds have potential to be used in patients with traumatic brain injury and neurodegenerative disorders.

STATEMENT OF FEDERALLY FUNDED RESEARCH

None.

BACKGROUND OF THE DISCLOSURE

Many diseases and disorders of the brain cause swelling of brain tissue also known as neuroinflammation. Neuroinflammation is beginning to be recognized as one of the hallmark signs and disease progression factors of Alzheimer's and Parkinson's disease. The swelling of brain tissue can limit the amount of blood flow to areas in the brain and can inhibit the body's natural disease fighting mechanisms. Traumatic brain injuries (TBI) also cause significant neuroinflammation. Unresolved and severe brain edema is the leading cause of death for TBI patients within the first few days of the injury.

Recent research efforts have made significant advancements in the area of treatment of neurodegenerative disorders. Neuroinflammation is widely regarded as chronic, as opposed to acute, inflammation of the central nervous system. Acute inflammation usually follows injury to the central nervous system immediately, and is characterized by inflammatory molecules, endothelial cell activation, platelet deposition, and tissue edema. Chronic inflammation is the sustained activation of glial cells and recruitment of other immune cells into the brain. It is chronic inflammation that is typically associated with neurodegenerative diseases.

Because neuroinflammation has been associated with a variety of neurodegenerative diseases, there is increasing interest to determine whether reducing inflammation will reverse neurodegeneration. Inhibiting inflammatory cytokines, such as IL-1β, decreases neuronal loss seen in neurodegenerative diseases. Current treatments for multiple sclerosis include interferon-B, Glatiramer acetate, and Mitoxantrone, which function by reducing or inhibiting T Cell activation, but have the side effect of systemic immunosuppression. In Alzheimer's disease, the use of non-steroidal anti-inflammatory drugs decreases the risk of developing the disease. Current treatments for Alzheimer's disease include NSAIDs and glucocorticoids. NSAIDs function by blocking conversion of prostaglandin H2 into other prostaglandins (PGs) and thromboxane (TX). Prostaglandins and thromboxane act as inflammatory mediators and increase microvascular permeability.

Certain receptors have been targeted for inhibition, including Histamine 1 (H1) and Dopamine Transporter (DAT), as well as Histamine 2 (H2) and 5-HT2C receptors. However, there is a need in the art to develop effective treatments for multiple inhibitions, while keeping side effects low.

SUMMARY OF THE DISCLOSURE

The present disclosure addresses failings in the art by providing compositions of substituted bisphenylalkylureas, and methods for a therapeutic treatment that is able to combat neuroinflammation caused by diseases and disorders such as Alzheimer's disease, Parkinson's disease and traumatic brain injury. Compound, 1-(5,5-bis(4-fluorophenyl)pentyl)-3-(4-chlorophenyl)urea, and related derivatives, referred to herein as substituted bisphenylalkylureas, act by blocking at least two receptors in the brain that contribute to the increase in inflammation. The 2 receptors, Histamine 1 (H1) and Dopamine Transporter (DAT), are both blocked by the same composition of the present disclosure, and this ability leads to a greater decrease in brain edema.

It is therefore an object of the present disclosure to enable reduction of neuroinflammation by inhibition of one or more of the H1 receptor, H2 receptor, dopamine transporter (DAT), and/or 5HT3C receptor.

In one aspect, the present disclosure provides a compound of substituted bisphenylalkylureas, or a pharmaceutically acceptable salt thereof. In another aspect, the present disclosure provides a compound comprising Formula I (see FIG. 1). In another aspect, the present disclosure provides a compound comprising Formula II (see FIG. 2). In another aspect, the present disclosure provides a compound comprising Formula III (see FIG. 3). In another aspect, the compound may be a pharmaceutically acceptable salt thereof, and wherein R in Formulas II and III may be independently be an electron-withdrawing group or electron-donating group. In another aspect, R may be independently be an electron-withdrawing group selected from a group consisting of: Cl, CF3, NO2, and combinations thereof. In yet another aspect, R may be independently be an electron-donating group selected from a group consisting of: alkyl, hydroxyl, ether, substituted amines, primary amines, and combinations thereof. In such case, the phenyl group on both rings may comprise F— as a substituent.

It is another object of the present invention to provide a method for reducing neuroinflammation to treat a disease causing neuroinflammation, said method comprising administering to the patient a therapeutically effective amount of a compound of Formula I, Formula II, Formula III, or a pharmaceutically acceptable salt thereof. Said compounds decrease neuroinflammation by acting on one or more of Alzheimer's disease, Parkinson's disease, and traumatic brain injury. The compounds set forth in the present invention decrease neuroinflammation by inhibiting H1 and H2 receptors.

In another aspect said compounds represented as Formula I, Formula II, and Formula III comprises an aqueous solution and one or more pharmaceutically acceptable excipients, additives, carriers or adjuvants. Said compounds may further comprise one or more excipients, carriers, additives, adjuvants, or binders in a tablet or capsule. In yet another aspect the compound may be administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, or vaginal route.

It is another aspect of the present invention that the compounds represented as Formula I, Formula II, and Formula III inhibit dopamine transporter (DAT). In another aspect, such DAT inhibition therefore decreases neuroinflammation by inhibiting dopamine transporter (DAT). In another aspect, the compounds decrease neuroinflammation by acting on the 5-HT2C receptor. In another aspect, the compounds decrease neuroinflammation by inhibiting H1 receptor, H2 receptor, dopamine transporter (DAT), and/or 5HT3C receptor.

In another aspect of the present disclosure, a method is provided for reducing neuroinflammation to treat a disease causing neuroinflammation in a patient comprising administering to the patient a compound which is a substituted bisphenylalkylurea, or a pharmaceutically acceptable salt thereof, or Formula I, Formula II, or Formula III, or pharmaceutically acceptable salts thereof. In another aspect, the said compound decreases neuroinflammation by acting on one or more of Alzheimer's disease, Parkinson's disease, traumatic brain injury, and brain tumors. In another aspect the compound decreases neuroinflammation by inhibiting H1 and H2 receptors.

In another aspect the compound comprises an aqueous solution and one or more pharmaceutically acceptable excipients, additives, carriers or adjuvants. In another aspect the compound further comprises one or more excipients, carriers, additives, adjuvants, or binders in a tablet or capsule.

In another aspect the compound is administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, or vaginal route.

In another aspect the compound decreases neuroinflammation by inhibiting dopamine transporter (DAT). In another aspect the compound decreases neuroinflammation by acting on the 5-HT2C receptor. In another aspect the compound compound decreases neuroinflammation by inhibiting H1 receptor, H2 receptor, dopamine transporter (DAT), and/or 5HT3C receptor.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure.

DETAILED DESCRIPTION OF THE DISCLOSURE

Figure 1:
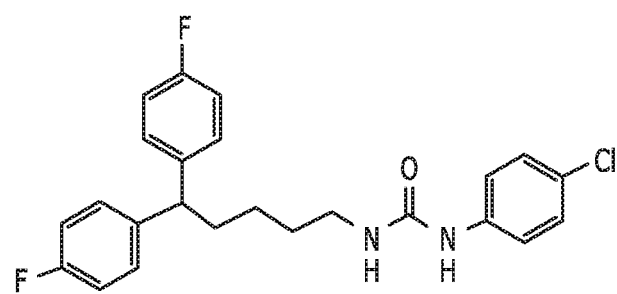
FIG. 1 depicts Formula I.

While the making and using of various embodiments of the present disclosure are discussed in detail below, it should be appreciated that the present disclosure provides many applicable inventive concepts that can be embodied in a wide variety of specific contexts, goods, or services. The specific embodiments discussed herein are merely illustrative of specific ways to make and use the disclosure and do not delimit the scope of the disclosure.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The present disclosure will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, compositions, or systems. Accordingly, embodiments may, for example, take the form of methods, compositions, compounds, materials, or any combination thereof. The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The term "treating" refers to reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a compound or composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

The terms "subject", "individual", or "patient" are used interchangeably herein and refer to an animal preferably a warm-blooded animal such as a mammal. Mammal includes without limitation any members of the Mammalia. In general, the terms refer to a human. The terms also include domestic animals bred for food or as pets, including equines, bovines, sheep, poultry, fish, porcines, canines, felines, and zoo animals, goats, apes (e.g. gorilla or chimpanzee), and rodents such as rats and mice.

Figure 2:
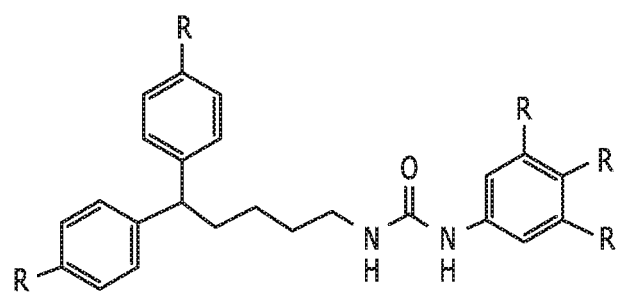
FIG. 2 depicts Formula II.
Figure 3:
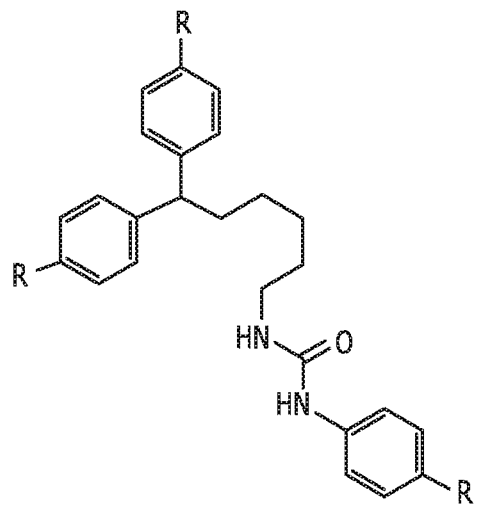
FIG. 3 depicts Formula III.

A compound of the Formula I, II, or III (see FIGS. 1, 2, and 3) can exist in unsolvated as well as solvated forms with pharmaceutically acceptable solvents such as water, ethanol, and the like. The solvated forms may be considered equivalent to the unsolvated forms for the purposes of the present invention.

"Therapeutically effective amount" relates to the amount or dose of an active compound of the Formula I, II, or III, or a composition comprising the same, that will lead to one or more desired effects, in particular, one or more therapeutic effects, more particularly beneficial effects. A therapeutically effective amount of a substance can vary according to factors such as the disease state, age, sex, and weight of the subject, and the ability of the substance to elicit a desired response in the subject. A dosage regimen may be adjusted to provide the optimum therapeutic response (e.g. sustained beneficial effects). For example, several divided doses may be administered daily or the dose may be proportionally reduced as indicated by the exigencies of the therapeutic situation.

The term "pharmaceutically acceptable carrier, excipient, or vehicle" refers to a medium which does not interfere with the effectiveness or activity of an active ingredient and which is not toxic to the hosts to which it is administered. A carrier, excipient, or vehicle includes diluents, binders, adhesives, lubricants, disintegrates, bulking agents, wetting or emulsifying agents, pH buffering agents, and miscellaneous materials such as absorbents that may be needed in order to prepare a particular composition. Examples of carriers etc. include but are not limited to saline, buffered saline, dextrose, water, glycerol, ethanol, and combinations thereof. The use of such media and agents for an active substance is well known in the art.

It is therefore an embodiment of the present disclosure to provide novel derivative compounds of urea for reducing neuroinflammation in a patient, wherein compounds of Formula I, Formula II, and Formula III are presented. In one aspect Formula I is provided (see FIG. 1). It is another embodiment of the present disclosure to provide a compound of Formula II (see FIG. 2). It is another embodiment of the present disclosure to provide a compound of Formula III (see FIG. 3). In references to FIGS. 2 and 3, "R" may be independently be electron withdrawing groups, such as Cl, CF3, NO2, among others. "R" may further independently be, or electron-donating, such as alkyl, hydroxyl, ether, amines (substituted and primary) and others. Phenyl groups have an F— as a substituent on both rings.

It is another embodiment of the present disclosure to provide pharmaceutically acceptable compositions comprising compounds of Formula I, II, and II, and a pharmaceutically acceptable carrier.

In one embodiment, the compounds, compositions, and methods disclosed herein act to restore dopamine levels in a patient to a level required for proper brain function. This is accomplished by inhibition of the dopamine transporter (DAT). The DAT is a significant focus of many therapies, as it mediates uptake of dopamine into neurons. Dopamine reuptake via DAT provides the primary mechanism through which dopamine is cleared from synapses, upon which the signal of the neurotransmitter is terminated. Dopamine therefore is relevant to multiple aspects of cognition, and the DAT facilitates regulation of this signal. The impetus for DAT-mediated dopamine re-uptake is the ion concentration gradient generated. The compounds, compositions, and methods disclosed therefore or capable of maintaining dopamine levels in a patient, which provides a key feature of treatment of many neurological disorders, including neuroinflammatory conditions.

In another embodiment, the compounds, compositions, and methods disclosed herein therefore may be utilized to prevent and/or treat a disease involving neuroinflammation. Neuroinflammation is a characteristic feature of disease pathology and progression in a diverse array of neurodegenerative disorders, including inter alia, Alzheimer's disease, Parkinson's disease and traumatic brain injury. Additional conditions include amyotrophic lateral sclerosis, autoimmune disorders, priori diseases, dementia, cerebral atrophy, frontotemporal lobal degeneration, Lewy Body disease, Huntington's disease, stroke, and other response conditions involving chronic or excessive activation of the production of proinflammatory cytokines and chemokines, oxidative stress-related enzymes, and acute phase linkage of glial activation.

In an illustrative embodiment of the present disclosure, an agent compound of the present disclosure, referred to herein as compound Formula I (AZ2-57), was presented for treatment of Parkinson's disease. Hallmark conditions of Parkinson's disease include symptoms such as (1) Chronic inflammation; (2) Presence of proteinaceous inclusions—Lewy bodies; and (3) Progressive degeneration of dopaminergic neurons in the Substantia Nigra pars compacta. Inflammation applies to this disease state in various capacities. The immune system is involved from the earlier stage of disease and immune factor is not just an outcome of disease, but one of the reasons. NSAIDS users traditionally have lower incidents of Parkinson's disease. Inflammation preferentially destroys dopamine neurons in the presence of GABA- and serotonin receptors. Further, blood-brain barrier (BBB) integrity declines with age. Parkinson's patients have disrupted BBB integrity that favors permeation of immune cells into the brain parenchyma, inducing progressive degeneration of the dopamine receptors. Therefore, Parkinson's disease is characterized by dramatic depletion of striatal dopamine levels. For four decades L-DOPA (alt., L-3,4-dihydroxyphenylalanine) (a precursor of dopamine) is used as treatment of Parkinson's disease. However, motor complication issues are related to L-DOPA chronic treatment, including: shortening of benefits' duration; wearing-off; and dyskinesia.

In addressing the use of the compounds of the present disclosure, Dopamine Transporter (DAT) inhibition is facilitated. In doing so, increased time is spent by dopamine in the synaptic cleft. Further, DAT inhibition potentiates L-DOPA therapeutic effect, and alleviates L-DOPA induced dyskinesia.

Figure 4:
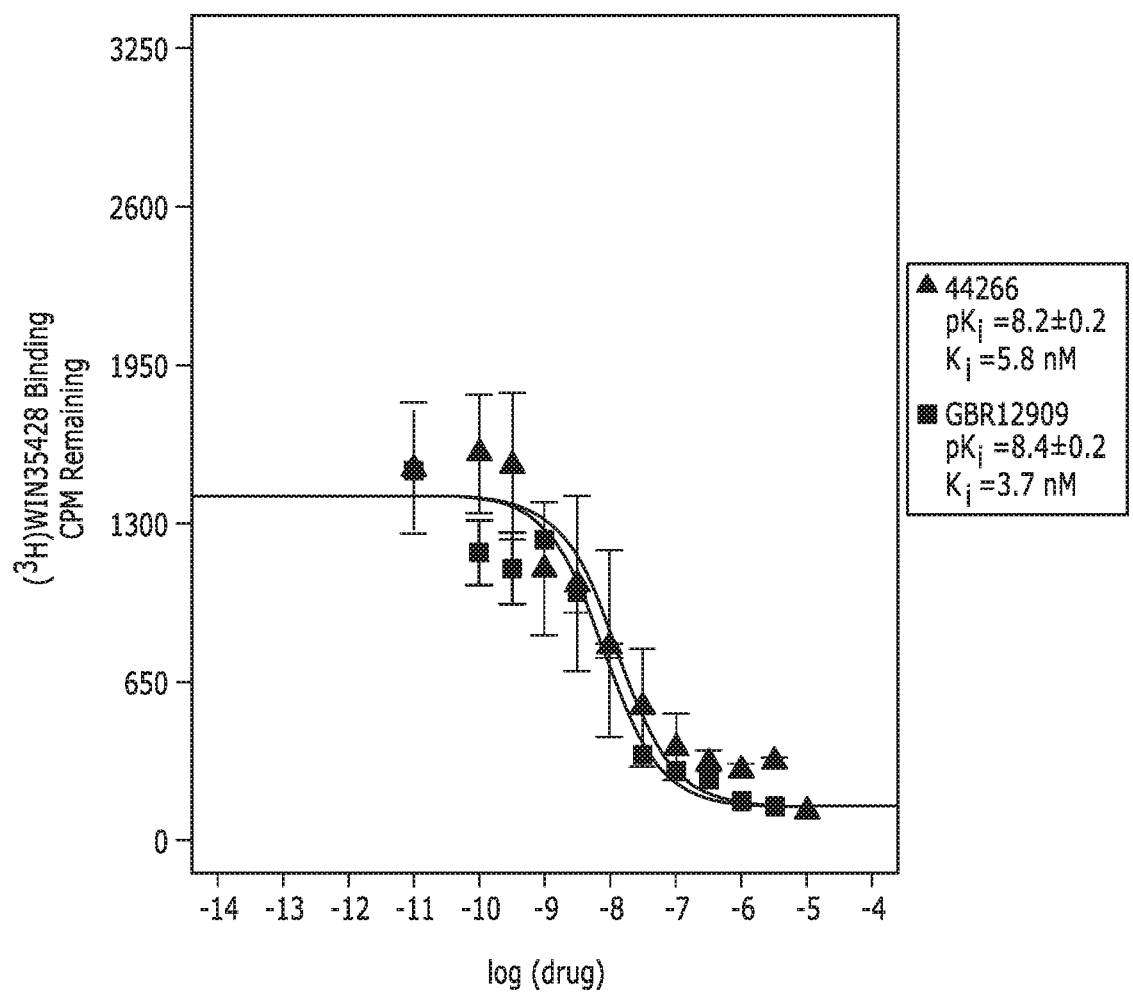
FIG. 4 depicts a graph showing DAT inhibition (Ki) of compound of the present disclosure designated Formula I (AZ2-57).

In one embodiment, compound of the present disclosure Formula I (AZ2-57) is shown in in vitro studies to show DAT inhibition (see FIG. 4). The compound has Ki of 5.2 nm at DAT, one of the lowest among the art.

Figure 5:
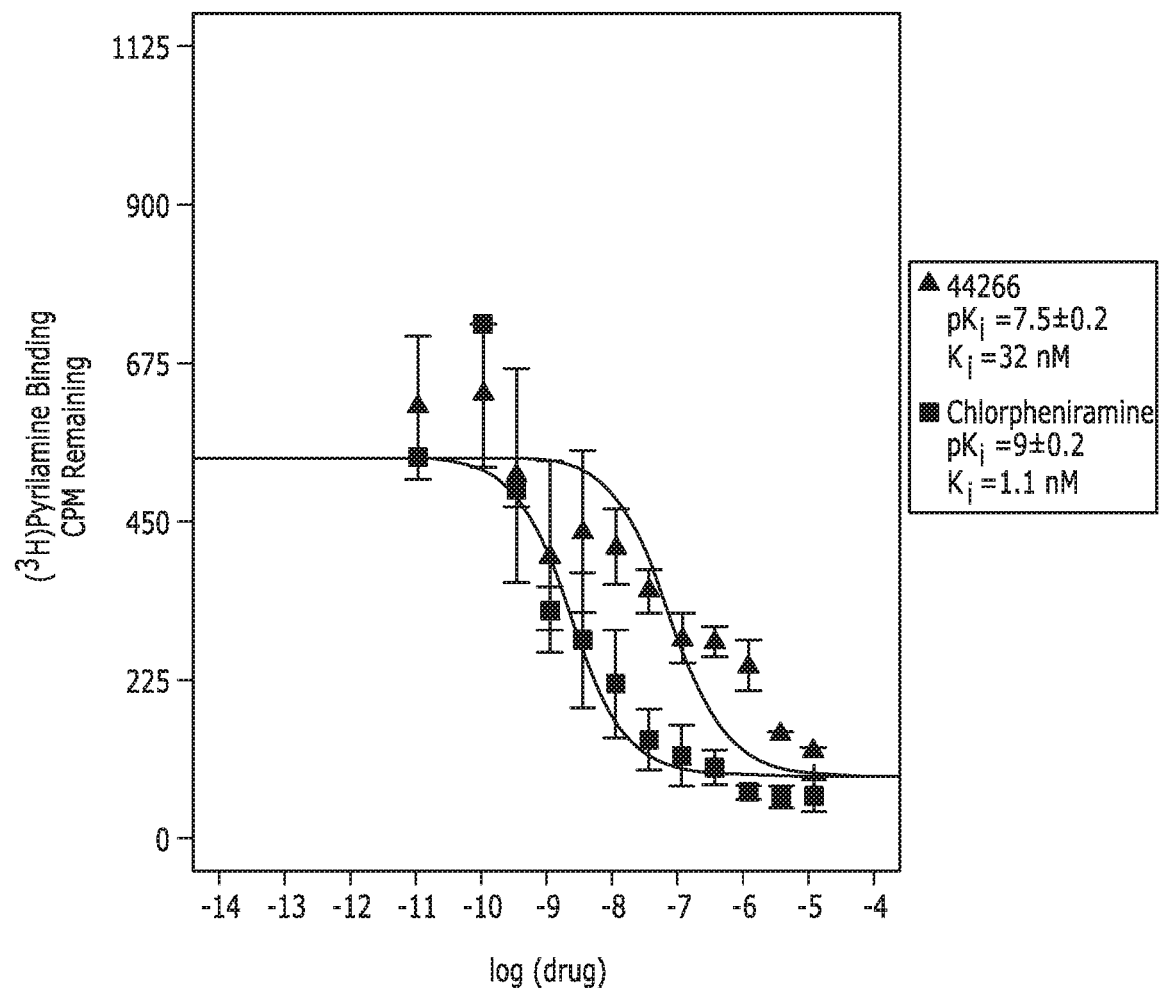
FIG. 5 depicts a graph showing H1 R inhibition (Ki) of compound of the present disclosure designated as Formula I (AZ2-57).
Figure 6:
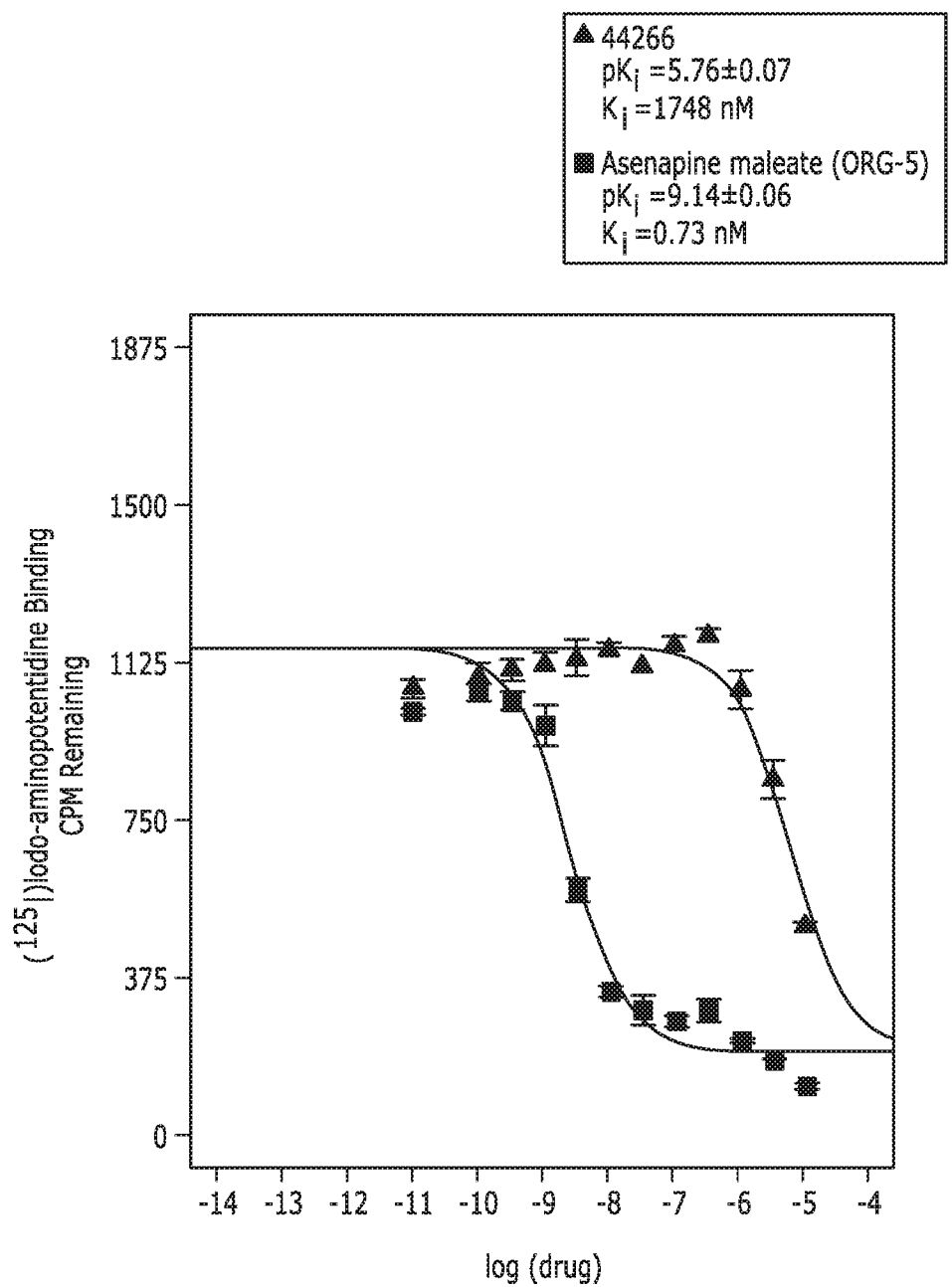
FIG. 6 depicts a graph showing H2 R inhibition (Ki) of compound of the present disclosure designated as Formula I (AZ2-57).

Further compound shown as Formula I (AZ2-57), inhibits the H1 receptor, and as shown in FIG. 5, such inhibition suggests 65.4% inhibition (@Ki=32 nM). 54% of the H2 receptor is also shown by compound Formula 1 (AZ2-57) (@Ki=1748 nM (see FIG. 6). Therefore compound Formula I (AZ2-57) of the present disclosure is further capable of inhibition of Histamine-related pathways and can be used as a dual DAT-inhibitor/anti-inflammatory agent in the treatment of Parkinson's disease.

Figure 7:
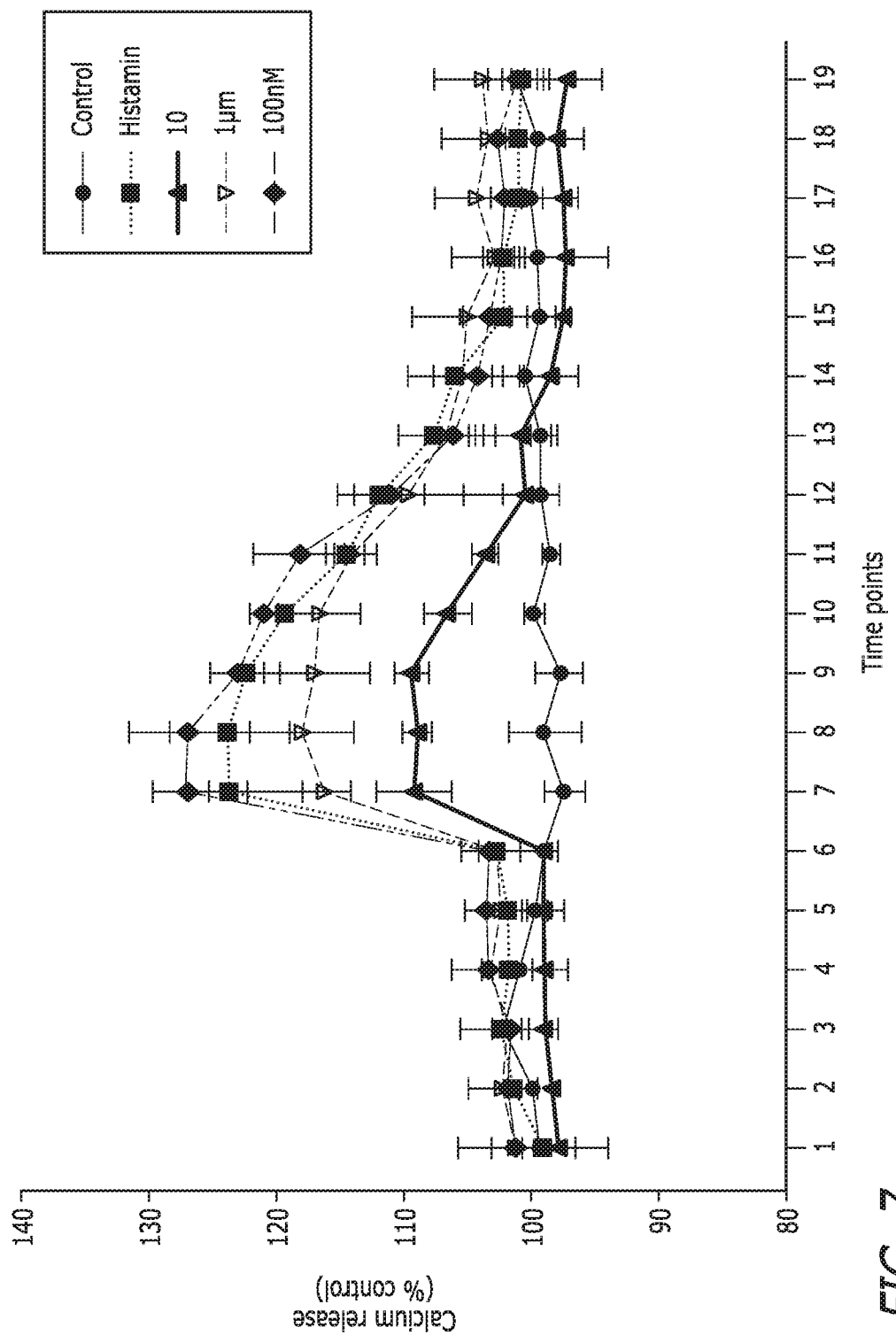
FIG. 7 depicts a graph showing Ca2+ release assay (HUVEC cells) of compound of the present disclosure designated as Formula I (AZ2-57).

Compound ZX2-57 further showed CA2+ release to be effectively manipulated by a compound of the present disclosure (see FIG. 7). Unlike many other DAT inhibitors on the market, our compound has very limited interaction with other GPCR receptors, reducing potential CNS-induced toxicity. It is thus an embodiment of the present disclosure to further show effect on microglia-induced immune response (chronic inflammation), dopamine surge in the presence of Formula I (AZ2-57).

Figure 8:
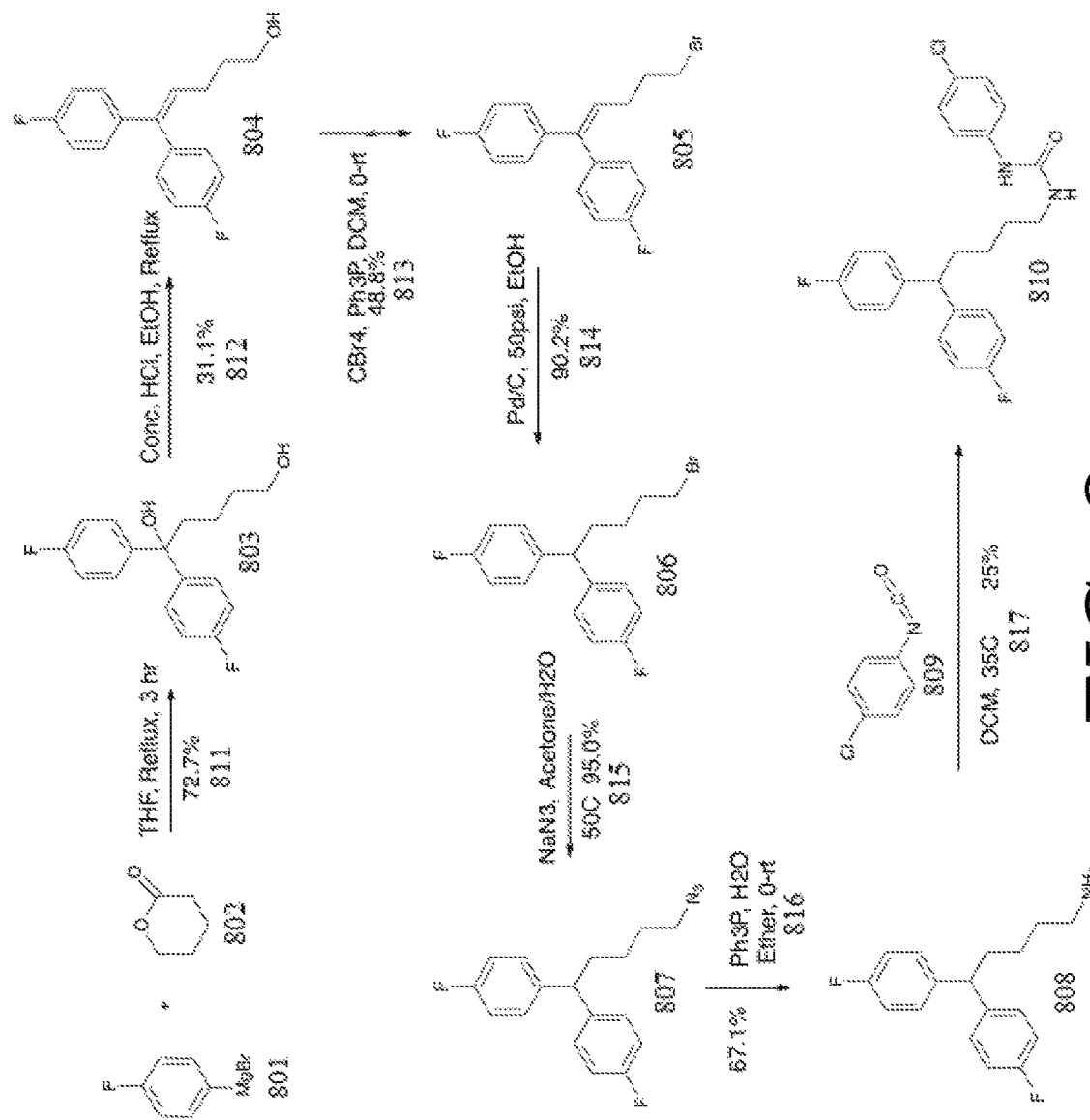
FIG. 8 is a schematic of a process to synthesize of an embodiment of the present invention.

FIG. 8 shows an example of a process for synthesizing 1-(5,5-bis(4-fluorophenyl)pentyl)-3-(4-chlorophenyl)urea (compound 810). In step 811, 2M 4-fluorophenyl magnesium bromide (compound 801) in ether (25 ml, 50 mmol) was taken in a dry two neck 100 ml round bottom flask under nitrogen environment. Delta valerolactone (compound 802) (2 g, 20 mmol) was dissolved in 20 ml THF dropwise and added to the reaction mixture. The reaction mixture was refluxed for 3 hours. Upon completion, the reaction was quenched with HCl (aq), followed by removal of THF using a rotary evaporator. The crude product was extracted using diethyl ether (3×15 ml). The combined organic portion was washed with brine solution, dried over anhydrous sodium sulfate, filtered and evaporated to dryness. The crude product was purified by chromatography using silica gel and hexane: ethyl acetate 30%-50%. Product (4.2 g, 72.7% yield) was obtained as a light yellow solid. 1H NMR (400 MHz, CHLOROFORM-d) δ ppm 1.35 (br d, J=7.58 Hz, 2H) 1.46-1.71 (m, 2H) 2.20-2.38 (m, 2H) 3.62 (t, J=6.36 Hz, 2H) 4.12 (t, J=7.09 Hz, 1H) 6.95-7.02 (m, 4H) 7.31-7.39 (m, 4H). This product was 1,1-bis(4-fluorophenyl)pentane-1,5-diol (compound 803).

In step 812, a reaction mixture containing,1-bis(4-fluorophenyl)pentane-1,5-diol (compound 803) (4.2 g, 14.5 mmol) and HCl (conc) (17 mL) in ethanol (200 mL) was refluxed for 12 hours. Upon completion, the reaction was neutralized using with NaHCO$_3$ and dried with Na$_2$SO$_2$. Filtration, evaporation in vacuo, and purification by flash chromatography (PE:EtOAc=3:1-1:1) afforded desired product in the form of light yellow liquid (1.25 g, 31.1%). 1H NMR (400 MHz, CHLOROFORM-d) 6 ppm −0.02--0.01 (m, 1H) 0.01-0.02 (m, 1H) 1.70 (dd, J=7.83, 6.85 Hz, 2H) 2.18 (d, J=7.34 Hz, 2H) 3.63 (t, J=6.48 Hz, 2H) 6.02 (t, J=7.45 Hz, 1H) 6.95 (t, J=8.10 Hz, 2H) 7.04-7.18 (m, 6H). This product was 5,5-bis(4-fluorophenyl)pent-4-en-1-ol (compound 804).

In step 813, Ph$_3$P (2.26 g, 8.64 mmol) was added to a solution of 5,5-bis(4-fluorophenyl)pent-4-en-1-ol (compound 804) (1.25 g, 4.55 mmol) in CBr$_4$ (1.8 g, 5.46 mmol) in dry CH$_2$Cl$_2$ (45 mL) at 0° C. The reaction mixture was allowed to warm to room temperature slowly. After stirring for 4 to 5 hours, the reaction was completed. The reaction mixture was filtrated, and washed using petroleum ether. Organic solvents were removed using a rotary evaporator, and the final product was purified using flash chromatography (EA:Hex=20:1-10:1) to afford 0.76 g (48.9%) of a liquid. $^1$H NMR (400 MHz, CHLOROFORM-d) 5 ppm 1.95-2.05 (m, 2H) 2.25 (q, J=7.34 Hz, 2H) 3.38 (t, J=6.72 Hz, 2H) 5.97 (t, 1H) 6.95 (t, J=8.11 Hz, 2H) 7.04-7.19 (m, 6H). This product was 4,4'-bis (5-bromopent-1-ene-1,1diyl) bis (flurobenzene) (compound 805).

In step 814, a solution of 4,4'-bis (5-bromopent-1-ene-1,1diyl)bis (flurobenzene) (compound 805) (0.760 g) and Pd—C (70 mg, 10%) in ethanol (30 mL) was stirred under hydrogen atmosphere (50 psi) overnight at room temperature. Upon reaction completion, the mixture was filtered through celite and concentrated in vacuo. The crude product was purified by flash chromatography (Hex:EA=30:1-115:1) to yield 0.684 g (90.1%) of a final product as a liquid. $^1$H NMR (400 MHz, CHLOROFORM-d) 5 ppm 1.39 (br d, J=7.34 Hz, 2H) 1.82-1.95 (m, 2H) 2.00 (br d, J=7.83 Hz, 2H) 3.36 (t, J=6.72 Hz, 2H) 3.86 (s, 1H) 6.97 (br t, J=8.68 Hz, 4H) 7.15 (br dd, J=8.19, 5.50 Hz, 4H). This product was 4,4'-(5-bromopentane-1,1-diyl)bis(fluorobenzene) (compound 806).

In step 815, NaN$_3$ (0.150 g, 1.87 mmol, 5 equiv.) was added to a solution of 4,4'-(5-bromopentane-1,1-diyl)bis (fluorobenzene) (compound 806) (0.120 g, 0.37 mmol, 1 equiv.) in 2 ml of acetone. Water was added dropwise with shaking until NaN$_3$ dissolved entirely and made a clear solution. Then the reaction mixture was kept stirring at 45° C. for 24 hours. The reaction was followed by TLC and reaction solvent was removed upon reaction completion. Resulted residue was dissolved in water and extracted using chloroform to obtain 0.101 g (95.1%) of the final product. $^1$H NMR (400 MHz, CHLOROFORM-d) δ ppm 1.31 (m, 2H) 1.57-1.67 (m, 2H) 2.01 (dd, J=7.83 Hz, 2H) 3.23 (t, J=6.97 Hz, 2H) 3.86 (t, 1H) 6.94-7.01 (m, 4H) 7.12-7.18 (m, 4H). This product was 4,4'-(5-azidopentane-1,1-diyl)bis (fluorobenzene) (compound 807).

In step 816, Ph$_3$P (0.130 g, 0.498 mmol, 1.5 equiv.) was added to a solution of compound 7 (0.100 g, 0.332 mmol, 1 eq) in dry di-ethyl-ether (2.5 ml) at 0□C and stirred for 3 hours 0° C. Water (0.05 ml) was added to the reaction vessel and stirred overnight at room temperature. Upon full consumption of azide, the reaction solvent was removed, and formed residue was purified using flash chromatography (0-10% MeOH in DCM+ 0.1% TEA) to obtain 0.061 g (67%) of the desired product. $^1$H NMR (400 MHz, CHLOROFORM-d) δ ppm 1.26 (m, 2H) 1.37-1.60 (m, 2H) 1.98 (q, 2H) 2.56-2.78 (t, 2H) 3.85 (t, 1H) 6.95 (m, 4H) 7.05-7.26 (m, 4H). This product was 5,5-bis(4-fluorophenyl)pentan-1-amine (compound 808).

In step 817, 1-chloro-4-isocyanatobenzene (compound 809) (0.016 g, 0.11 mmol, 1 equiv.) was added to the solution of 5,5-bis(4-fluorophenyl)pentan-1-amine (compound 808) (0.030 g, 0.11 mmol, 1 equiv.) in DCM (4 ml) and stirred under an inert environment at 35° C. for 4 hours. The reaction was monitored using TLC (5% EA in DCM, Rf=0.3). Upon completion, the reaction solvent was removed in vacuum and the final product was obtained upon crystallization in the ether (0.012 g (25%), white powder). $^1$H NMR (400 MHz, CHLOROFORM-d) δ ppm 1.13-1.37 (m, 2H) 1.42-1.59 (m, 2H) 1.97 (br d, J=7.83 Hz, 2H) 3.16 (br d, J=6.11 Hz, 2H) 3.82 (s, 1H) 4.77 (s, 1H) 6.52 (s, 1H) 6.86-7.04 (m, 4H) 7.07-7.28 (m, 8H) 13C NMR (101 MHz, CHLOROFORM-d) δ ppm 25.16 (s, 1C) 29.96 (s, 1C) 35.47 (s, 1C) 40.16 (s, 1C) 49.66 (s, 1C) 115.20 (s, 1C) 115.40 (s, 1C) 121.87 (s, 1C) 128.77 (s, 1C) 129.02 (s, 1C) 129.09 (s, 1C) 129.23 (s, 1C) 137.15 (s, 1C) 140.39 (s, 1C) 140.42 (s, 1C) 155.41 (s, 1C) 160.12 (s, 1C) 162.55 (s, 1C). This final product was 1-(5,5-bis(4-fluorophenyl)pentyl)-3-(4-chlorophenyl)urea (compound 810).

It is another embodiment of the present disclosure to provide one of Formulas I, II, or III comprising an aqueous solution and one or more pharmaceutically acceptable excipients, additives, carriers or adjuvants. Formula I, II, or III may further comprise one or more excipients, carriers, additives, adjuvants, or binders in a tablet or capsule. Formulas I, II, or III may further be administered via an oral, intraperitoneal, intravascular, peripheral circulation, subcutaneous, intraorbital, ophthalmic, intraspinal, intracisternal, topical, infusion, implant, aerosol, inhalation, scarification, intracapsular, intramuscular, intranasal, buccal, transdermal, pulmonary, rectal, or vaginal route.

The compounds of the present disclosure are capable of treatment in a manner selective to CNS activity and does not manipulate the activity of other CNS receptors, as other CNS drugs have a tendency to do. Therefore, the compounds of the present disclosure have substantially reduced toxicity profiles (i.e. depression, headache, suicidal thoughts, and the like). The compounds are further active as low nanomolar ranges due to its potency.

Those skilled in the art will recognize that the methods and compositions of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among various software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad combinations are possible in achieving the functions, features, and preferences described herein. Moreover, the scope of the present disclosure covers conventionally known manners for carrying out the described features as well as those variations and modifications that may be made to the processes, composition, or compounds described herein as would be understood by those skilled in the art now and hereafter.

While various embodiments have been described for purposes of this disclosure, such embodiments should not be deemed to limit the teaching of this disclosure to those embodiments. Various changes and modifications may be made to the elements and operations described above to obtain a result that remains within the scope of the compositions and methods described in this disclosure.

What is claimed is:

1. A compound having a formula selected from a group consisting of:

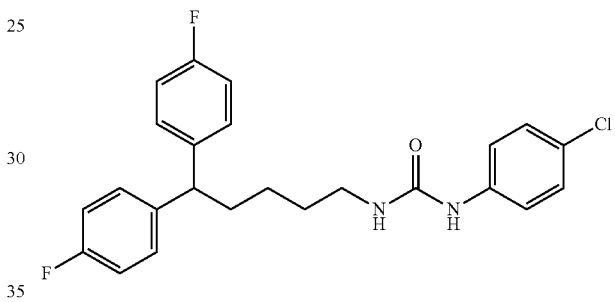

or a pharmaceutically acceptable salt thereof.

2. The compound of claim 1, wherein said compound decreases neuroinflammation by acting on one or more of Alzheimer's disease, Parkinson's disease, and traumatic brain injury.

3. The compound of claim 1, wherein said compound decreases neuroinflammation by inhibiting H1 and H2 receptors.

4. The compound of claim 1, wherein, wherein said compound comprises an aqueous solution and one or more pharmaceutically acceptable excipients, additives, carriers or adjuvants.

5. The compound of claim 1, wherein said compound further comprises one or more excipients, carriers, additives, adjuvants, or binders in a tablet or capsule.

* * * * *